United States Patent
Natsuyama et al.

(10) Patent No.: US 11,772,039 B2
(45) Date of Patent: Oct. 3, 2023

(54) GAS TREATMENT METHOD AND GAS TREATMENT APPARATUS

(71) Applicant: SEKISUI CHEMICAL CO., LTD., Osaka (JP)

(72) Inventors: Kazuto Natsuyama, Tsukuba (JP); Kokoro Hamachi, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 378 days.

(21) Appl. No.: 17/275,432

(22) PCT Filed: Sep. 25, 2019

(86) PCT No.: PCT/JP2019/037637
§ 371 (c)(1),
(2) Date: Mar. 11, 2021

(87) PCT Pub. No.: WO2020/067181
PCT Pub. Date: Apr. 2, 2020

(65) Prior Publication Data
US 2022/0047985 A1    Feb. 17, 2022

(30) Foreign Application Priority Data
Sep. 25, 2018  (JP) .................. 2018-179532

(51) Int. Cl.
*B01D 53/047* (2006.01)
*C01B 3/56* (2006.01)
*B01D 53/04* (2006.01)

(52) U.S. Cl.
CPC ....... *B01D 53/047* (2013.01); *B01D 53/0446* (2013.01); *B01D 2257/504* (2013.01)

(58) Field of Classification Search
CPC .. B01D 53/047; B01D 53/04; B01D 53/0446; B01D 2257/504; B01D 53/30;
(Continued)

(56) References Cited

U.S. PATENT DOCUMENTS

| 4,315,759 A | 2/1982 | Benkmann |
| 4,732,577 A | 3/1988 | Koizumi et al. |

(Continued)

FOREIGN PATENT DOCUMENTS

| CN | 102431967 A | 5/2012 |
| CN | 102834159 A | 12/2012 |

(Continued)

OTHER PUBLICATIONS

Extended European Search Report, dated Jun. 2, 2022, issued by the European Patent Office in European Application No. 19866257.9.

(Continued)

*Primary Examiner* — Frank M Lawrence, Jr.
(74) *Attorney, Agent, or Firm* — Sughrue Mion, PLLC (57) ABSTRACT

Generation of bubbles in an organic-substance production apparatus is suppressed. A gas treatment method including: an adsorption step of passing a source gas containing at least carbon dioxide and nitrogen through an adsorption unit for adsorbing carbon dioxide to reduce a carbon dioxide concentration in the source gas; a supply step of supplying the source gas whose carbon dioxide concentration has been reduced by the adsorption step to an organic-substance production apparatus; and a monitoring step of monitoring a carbon dioxide concentration and a nitrogen concentration in the source gas; wherein the adsorption step has an ability regulation step of enhancing an ability of the adsorption unit to reduce a carbon dioxide concentration in the source gas, when a total concentration of the carbon dioxide concentration and the nitrogen concentration monitored in the monitoring step exceeds a threshold value.

10 Claims, 5 Drawing Sheets

(58) Field of Classification Search
CPC ............ B01D 2256/16; B01D 2256/20; B01D 2259/40007; C12M 41/32; C01B 2203/0405; C01B 2203/046; C01B 2203/0485; C01B 2203/049; C01B 2203/0495; C01B 2203/147; C01B 3/56; Y02C 20/40; Y02P 20/151
USPC ...... 95/8, 11, 12, 96, 139; 96/108, 121, 111, 96/134
See application file for complete search history.

(56) References Cited

U.S. PATENT DOCUMENTS

| | | | |
|---|---|---|---|
| 2009/0259323 | A1 | 10/2009 | Kesavan et al. |
| 2010/0242722 | A1 | 9/2010 | Belanger et al. |
| 2014/0352531 | A1 | 12/2014 | Patel |
| 2017/0260552 | A1 | 9/2017 | Haas et al. |
| 2021/0024963 | A1* | 1/2021 | Shimizu .................... C12P 7/08 |

FOREIGN PATENT DOCUMENTS

| | | |
|---|---|---|
| CN | 105246576 A | 1/2016 |
| CN | 107789949 A | 3/2018 |
| JP | 58-30321 A | 2/1983 |
| JP | 60-155521 A | 8/1985 |
| JP | 07-68120 A | 3/1995 |
| JP | 08-56646 A | 3/1996 |
| JP | 08-117542 A | 5/1996 |
| JP | 2005-331862 A | 12/2005 |
| JP | 2012-183002 A | 9/2012 |
| JP | 2014-77060 A | 5/2014 |
| JP | 2017-164683 A | 9/2017 |
| JP | 2018-058042 A | 4/2018 |
| WO | 2010/111049 A1 | 9/2010 |

OTHER PUBLICATIONS

International Search Report for PCT/JP2019/037637, dated Dec. 24, 2019.
Communication, dated Jun. 29, 2022, issued by the China National Intellectual Property Administration in Chinese Application No. 201980058298.2.
Communication, dated Apr. 8, 2021, issued by the International Bureau in International Application No. PCT/JP2019/037637.

* cited by examiner

GAS TREATMENT METHOD AND GAS TREATMENT APPARATUS

CROSS REFERENCE TO RELATED APPLICATIONS

This application is a National Stage of International Application No. PCT/JP2019/037637, filed Sep. 25, 2019, claiming priority based on Japanese Patent Application No. 2018-179532, filed Sep. 25, 2018.

FIELD

The present invention relates to a gas treatment method and a gas treatment apparatus for treating a source gas containing at least carbon dioxide and nitrogen.

BACKGROUND ART

A gasification method by thermal decomposition is known as a treatment method of industrial waste and general waste. This method thermally decomposes the waste to obtain a source gas containing carbon monoxide and hydrogen. The source gas can be used for various purposes. For example, Patent Document 1 leads a source gas into a culture tank housing a culture solution containing microorganisms to produce an organic substance, such as ethanol, by microbial fermentation.

Patent Document 1: JP2018-58042A

In an organic-substance production apparatus, such as a culture tank, which produces an organic substance from a source gas, bubbles are likely to generate on a liquid surface because of a reaction. When the bubbles excessively grow and enter an apparatus downstream of the organic-substance production apparatus, the bubbles may cause failure and/or contamination.

An object of the present invention is to treat a source gas such that generation of bubbles in an organic-substance production apparatus is suppressed.

SUMMARY

The present inventors have conducted intensive studies on carbon dioxide and nitrogen, which are not used at all or rarely used for producing an organic substance in the organic-substance production apparatus, in order to achieve the above object. The present inventors have found that the above object can be achieved by reducing a carbon dioxide concentration in a source gas, when a total concentration of carbon dioxide and nitrogen exceeds a threshold value, and have completed the present invention. Namely, the summary of the present invention is as follows.

[1] A gas treatment method comprising:
an adsorption step of passing a source gas containing at least carbon dioxide and nitrogen through an adsorption unit housing an adsorbent for adsorbing carbon dioxide to reduce a carbon dioxide concentration in the source gas;
a supply step of supplying the source gas whose carbon dioxide concentration has been reduced by the adsorption step to an organic-substance production apparatus that produces an organic substance; and
a monitoring step of monitoring a carbon dioxide concentration and a nitrogen concentration in the source gas before passing through the adsorption unit, a carbon dioxide concentration and a nitrogen concentration in the source gas after having passed through the adsorption unit, or a carbon dioxide concentration and a nitrogen concentration in the source gas having been supplied to the organic-substance production apparatus;
wherein the adsorption step has an ability regulation step of enhancing an ability of the adsorption unit to reduce a carbon dioxide concentration in the source gas, when a total concentration of the carbon dioxide concentration and the nitrogen concentration monitored in the monitoring step exceeds a threshold value.

[2] The gas treatment method described in [1], wherein:
the adsorption unit used in the adsorption step includes a first adsorption unit and a second adsorption unit that alternately perform an adsorption process for adsorbing carbon dioxide onto the adsorbent and a regeneration process for releasing the carbon dioxide adsorbed on the adsorbent, and
the ability regulation step shortens a switching cycle of the adsorption process and the regeneration process that are alternately performed by the first adsorption unit and the second adsorption unit, when the total concentration of the carbon dioxide concentration and the nitrogen concentration monitored in the monitoring step exceeds the threshold value.

[3] The gas treatment method described in [1] or [2], wherein:
the adsorption unit used in the adsorption step includes a first adsorption unit and a second adsorption unit that alternately perform an adsorption process for adsorbing carbon dioxide onto the adsorbent and a regeneration process for releasing the carbon dioxide adsorbed on the adsorbent, and
the ability regulation step lowers a flow rate of the source gas to be supplied to the adsorption unit including the first adsorption unit and the second adsorption unit, when the total concentration of the carbon dioxide concentration and the nitrogen concentration monitored in the monitoring step exceeds the threshold value.

[4] The gas treatment method described in any one of [1] to [3], wherein
the source gas is a synthetic gas further containing hydrogen and carbon monoxide.

[5] The gas treatment method described in [4], wherein
the organic substance is produced from the carbon monoxide and the hydrogen as raw materials.

[6] The gas treatment method according to described in any one of [1] to [5], wherein
the adsorption step reduces a carbon dioxide concentration in the source gas by a pressure swing adsorption method.

[7] A gas treatment apparatus for a source gas containing at least carbon dioxide and nitrogen, comprising:
an adsorption apparatus that reduces a carbon dioxide concentration in the source gas, the adsorption apparatus including an adsorption unit that houses an adsorbent for adsorbing carbon dioxide, an inlet unit that leads the source gas into the adsorption unit, and an outlet unit that leads the source gas out of the adsorption unit;
a supply apparatus that supplies the source gas whose carbon dioxide concentration has been reduced by the adsorption apparatus to an organic-substance production apparatus that produces an organic substance;
a monitoring unit that monitors a carbon dioxide concentration and a nitrogen concentration in the source gas before passing through the adsorption unit, or a carbon dioxide concentration and a nitrogen concentration in the source gas after having passed through the adsorption unit; and a control unit that controls the adsorption unit, the inlet unit or the outlet unit to enhance an ability of the adsorption unit to reduce a carbon dioxide concentration in the source gas, when a total concentration of the carbon dioxide concentration and the nitrogen concentration monitored by the monitoring unit exceeds a threshold value.

[8] The gas treatment apparatus described in [7], wherein:

the adsorption unit of the adsorption apparatus includes a first adsorption unit and a second adsorption unit that alternately perform an adsorption process for adsorbing carbon dioxide onto the adsorbent and a regeneration process for releasing the carbon dioxide adsorbed on the adsorbent; and the control unit shortens a switching cycle of the adsorption process and the regeneration process that are alternately performed by the first adsorption unit and the second adsorption unit, when the total concentration of the carbon dioxide concentration and the nitrogen concentration in the source gas before passing through the adsorption unit, the total concentration of the carbon dioxide concentration and the nitrogen concentration in the source gas after having passed through the adsorption unit, or a total concentration of a carbon dioxide concentration and a nitrogen concentration in the source gas having been supplied to the organic-substance production apparatus exceeds a threshold value.

[9] The gas treatment apparatus described in [7] or [8], wherein:

the adsorption unit of the adsorption apparatus includes a first adsorption unit and a second adsorption unit that alternately perform an adsorption process for adsorbing carbon dioxide onto the adsorbent and a regeneration process for releasing the carbon dioxide adsorbed on the adsorbent; and the control unit lowers a flow rate of the source gas to be supplied to the adsorption unit including the first adsorption unit and the second adsorption unit, when the total concentration of the carbon dioxide concentration and the nitrogen concentration in the source gas before passing through the adsorption unit, the total concentration of the carbon dioxide concentration and the nitrogen concentration in the source gas after having passed through the adsorption unit, or a total concentration of a carbon dioxide concentration and a nitrogen concentration in the source gas having been supplied to the organic-substance production apparatus exceeds a threshold value.

[10] The gas treatment apparatus described in any one of [7] to [9], wherein the adsorption unit reduces a carbon dioxide concentration in the source gas by a pressure swing adsorption method.

The present invention can treat a source gas such that generation of bubbles in an organic-substance production apparatus is suppressed.

DETAILED DESCRIPTION

An embodiment of the present invention is described herebelow with reference to the drawings. In the drawings attached to the specification, a scale dimension, an aspect ratio and so on are changed and exaggerated from the actual ones, for the convenience of easiness in illustration and understanding.

In an embodiment described below, a gas treatment apparatus is an apparatus that treats a source gas to regulate concentrations of various gases contained in the source gas, and supplies the treated source gas to an organic-substance production apparatus. The gas treatment apparatus is elaborated to treat the source gas such that generation of bubbles in the organic-substance production apparatus is suppressed. Herebelow, an example in which the gas treatment apparatus is applied to a gas treatment system that produces an organic substance from a source gas obtained by gasifying waste containing a carbon compound is described below. However, the gas treatment apparatus according to the embodiment is not only applied to the gas treatment system, but also can be applied various systems using a source gas.

Figure 1:
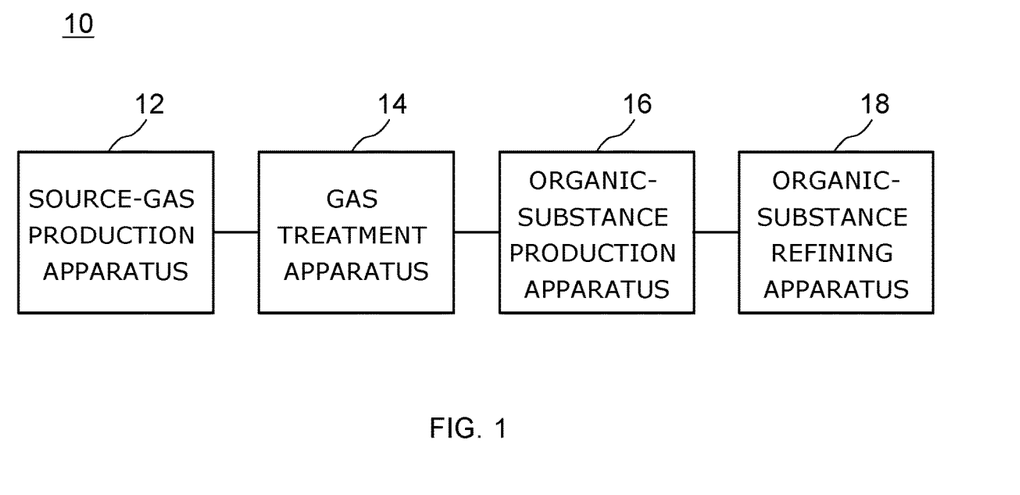
FIG. 1 is a view for describing an embodiment of the present invention, which is a block diagram for describing a schematic structure of a gas treatment system to which a gas treatment apparatus is applied.

The overall structure of a gas treatment system 10 is described first. As shown in FIG. 1, the gas treatment system 10 includes a source-gas production apparatus 12 that produces a source gas, a gas treatment apparatus 14 that treats the gas produced by the source-gas production apparatus 12, an organic-substance production apparatus 16 that reacts the gas treated by the gas treatment apparatus 14 to produce an organic substance, and an organic-substance refining apparatus that refines the organic substance produced by the organic-substance production apparatus 16.

The source-gas production apparatus 12 may be an apparatus that produces a source gas by gasifying a carbon source. A gasification furnace that burns (incompletely burns) a carbon source, such as a shaft furnace, a kiln furnace, a fluidized bed furnace or a gasification and reform furnace can be used as the source-gas production apparatus 12. A gasification furnace forming the source-gas production apparatus 12 is preferably of a fluidized bed type, because it partially burns waste to enable a high hearth load and excellent operability. When waste is gasified in a fluidized bed furnace at a low temperature (about 450 to 600° C.) in a low oxygen atmosphere, the waste is decomposed into char containing large amounts of gases (carbon monoxide, carbon dioxide, hydrogen, methane, etc.) and carbon. Further, since incombustibles contained in the waste are separated from a furnace bottom in a hygienic and low-oxidation state, valuable resources such as iron and aluminum in the incombustibles can be selectively recovered. Thus, such gasification of waste enables efficient resource recycling.

In the source-gas production apparatus 12 as a gasification furnace, a gasification temperature is typically 100° C. or more and 1500° C. or less, preferably 200° C. or more and 1200° C. or less. In the source-gas production apparatus 12 as a gasification furnace, a gasification reaction time is typically 2 seconds or more, preferably 5 seconds or more.

A carbon source put into the source-gas production apparatus 12 is not particularly limited. For example, various carbon-containing materials such as coal used in a coke oven of an iron mill, a blast furnace (blast furnace gas), converter or a coal-fired power plant, general waste and industrial waste introduced into an incinerator (especially gasifier), and carbon dioxide produced by various industries as a by-product, can be suitably utilized for the purpose of recycling. In more detail, the carbon source may include plastic waste, garbage, municipal waste (MSW), waste tires, biomass waste, household waste such as blankets and paper, waste such as building material, coal, petroleum oil, petroleum-derived compounds, natural gas, shale gas, etc. Among them, various wastes are preferred, and unsorted municipal waste is more preferred from the viewpoint of separation cost.

A source gas obtained by gasifying the carbon source contains carbon monoxide and hydrogen, in combination with the organic-substance production apparatus 16 described later. In particular, in combination with the organic-substance production apparatus 16 described later, it is preferable that a source gas containing a large amount of carbon monoxide is produced by a heat treatment (commonly known as gasification) that burns (incompletely burns) the carbon source, i.e., that partially oxidizes the carbon source. The source gas further contains carbon dioxide and nitrogen. The source gas may further contain, as still other components, soot, tar, nitrogen compounds, sulfur compounds, aromatic compounds, etc.

Next, the gas treatment apparatus 14 that treats the source gas produced by the source-gas production apparatus 12 is described. The gas treatment apparatus 14 treats the source gas produced by the source-gas production apparatus 12 so as to be suitable for use in the downstream organic-substance production apparatus 16. For example, the gas treatment apparatus 14 treats the source gas to suitably regulate concentrations of various gases contained in the source gas. In addition, the gas treatment apparatus 14 may remove or reduce specific substances such as various pollutants, soot dust particles, impurities, and compounds of unfavorable amounts. The gas treatment apparatus 14 may include one or more of a gas chiller (moisture separation apparatus), a separation apparatus of a low-temperature separation method (deep cooling method), a particle (soot) separation apparatus such as a cyclone or a bug filter, a scrubber (water-soluble impurity separation apparatus), a desulfurization apparatus (sulfide separation apparatus), a separation apparatus of a membrane separation method, a deoxidation apparatus, a separation apparatus of a pressure swing adsorption method (PSA), a separation apparatus of a temperature swing adsorption method (TSA), a separation apparatus of a pressure temperature swing adsorption method (PTSA), a separation apparatus using activated carbon, a separation apparatus using a palladium catalyst, etc.

Figure 2:
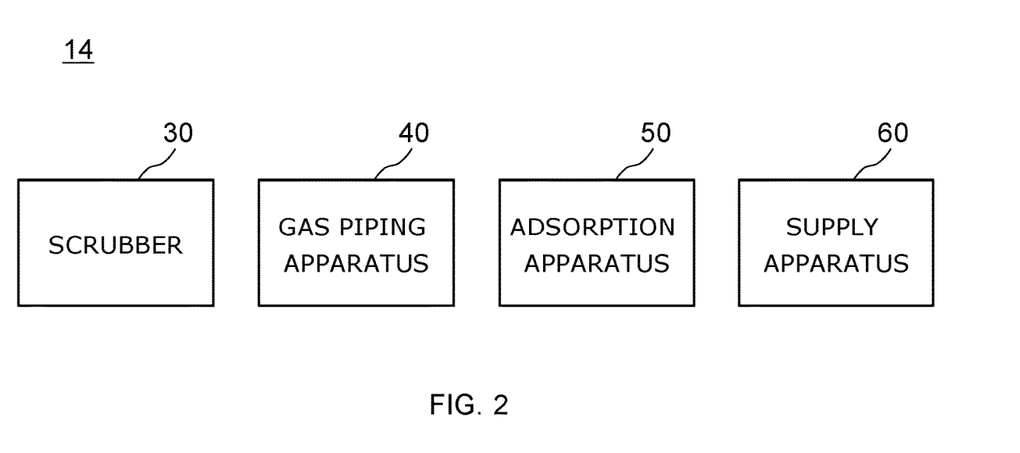
FIG. 2 is a block diagram for describing a schematic structure of the gas treatment apparatus of the gas treatment system of FIG. 1.

In the example shown in FIG. 2, the gas treatment apparatus 14 includes a scrubber 30, a gas piping apparatus 40 configured as a moisture separation apparatus, an adsorption apparatus 50 and a supply apparatus 60.

The scrubber 30 is used to remove pollutants in the source gas. Either a wet cleaning method or a dry cleaning method can be adopted depending on a purpose of the scrubber 30. Among them, the wet cleaning method performed by bringing a particulate substance into contact with a cleaning liquid can be suitably used. For example, a cleaning method using a so-called water curtain can be adopted. When the wet cleaning method is adopted, the cleaning liquid may be water, an acidic solution, an alkaline solution, etc., but water is preferred. A temperature of the cleaning liquid is usually 40° C. or less, preferably 30° C. or less, more preferably 25° C. or less, further preferably 15° C. or less.

The gas piping apparatus 40 serving as a moisture separation apparatus cools the source gas treated by the scrubber 30 to remove moisture from the source gas.

The adsorption apparatus 50 has a function of adsorbing carbon dioxide in the source gas. The adsorption apparatus 50 has at least any one of a PSA, a TSA and a PTSA. In this embodiment, an example in which the adsorption apparatus 50 has a PSA is described. The adsorption apparatus 50 may have a function of adsorbing a gas other than carbon dioxide.

Figure 3:
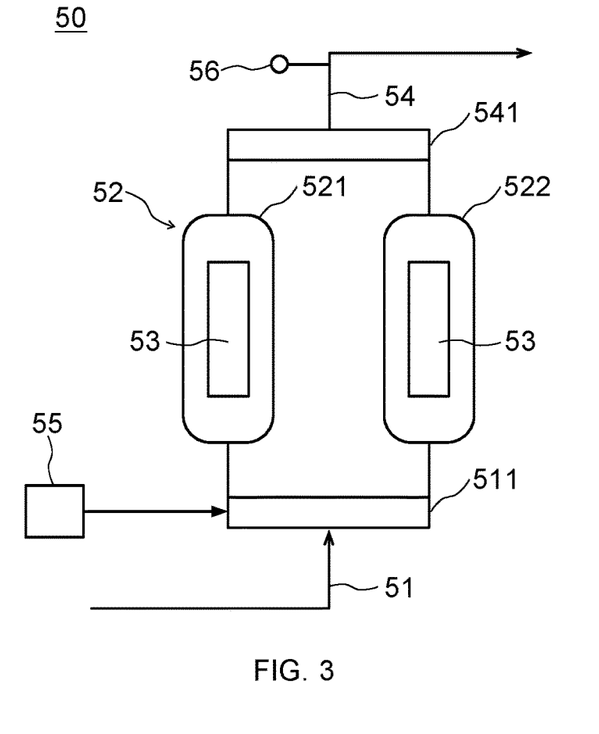
FIG. 3 is a view diagrammatically showing an example of adsorption apparatus of the gas treatment system of FIG. 1.

FIG. 3 is a view diagrammatically showing an example of the adsorption apparatus 50. The adsorption apparatus 50 has an inlet unit 51, an adsorption unit 52 including a first adsorption unit 521 and a second adsorption unit 522, an outlet unit 54, a control unit 55 and a monitoring unit 56.

The inlet unit 51 leads a pressurized source gas into the adsorption unit 52. In the example shown in FIG. 3, the inlet unit 51 includes an inlet-side switching unit 511 that switches a flow path of the source gas such that the pressurized source gas is lead into any one of the first adsorption unit 521 and the second adsorption unit 522 of the adsorption unit 52.

Each of the first adsorption unit 521 and the second adsorption unit 522 of the adsorption unit 52 houses an adsorbent 53 for adsorbing carbon dioxide. A porous material such as activated carbon, zeolite or molecular sieves, or an aqueous solution such as an amine solution can be used as the adsorbent 53.

The first adsorption unit 521 and the second adsorption unit 522 alternately perform an adsorption process and a regeneration process. The adsorption process is a process for adsorbing carbon dioxide onto the adsorbent in a pressurized environment. The regeneration process is a process for releasing the carbon dioxide adsorbed on the adsorbent in a depressurized environment. The aforementioned inlet unit 51 leads the source gas into one of the first adsorption unit 521 and the second adsorption unit 522 where the adsorption process is to be performed.

The outlet unit 54 leads the source gas after having passed through the adsorption unit 52 to the downstream side. In the example shown in FIG. 3, the outlet unit 54 includes an outlet-side switching unit 541 that switches the flow path of the source gas such that the source gas, which have passed through one of the first adsorption unit 521 and the second adsorption unit 522 where the adsorption process is performed, is lead to the downstream side.

The control unit 55 controls the inlet-side switching unit 511 to switch the flow path of the inlet unit 51, such that the first adsorption unit 521 and the second adsorption unit 522 alternately perform the adsorption process and the regeneration process. In addition, the control unit 55 controls the outlet-side switching unit 541 such that the source gas, which have passed through one of the first adsorption unit 521 and the second adsorption unit 522 where the adsorption process is performed, is lead to the downstream supply apparatus 60.

The supply apparatus 60 supplies the source gas whose carbon dioxide concentration has been reduced by the adsorption apparatus 50 to the organic-substance production apparatus 16. A carbon monoxide concentration, a hydrogen concentration, a carbon dioxide concentration and a nitrogen concentration in the source gas, which is supplied by the supply apparatus 60 of the gas treatment apparatus 14 to the organic-substance production apparatus 16, are, for example, 35 to 45% by volume, 35 to 45% by volume, 5 to 15% by volume and 5 to 15% by volume, respectively. The supply apparatus 60 includes, for example, a pipe connecting the adsorption apparatus 50 and the organic-substance production apparatus 16 to each other. In addition, the supply apparatus 60 may include a regulation unit that regulates a flow rate of the source gas to be supplied to the organic-substance production apparatus 16 per unit time. The regulation unit includes a valve, for example.

Next, the organic-substance production apparatus 16 is described. The organic-substance production apparatus 16 manufactures an organic substance by fermenting the source gas with microorganisms or by bringing the source gas into contact with a metal catalyst. Examples of an organic substance obtained by microbial fermentation of the source gas or a metal catalyzed reaction of the source gas may be methanol, ethanol, 2, 3-butaediol, acetic acid, lactic acid, isoprene, butadiene, etc. Among them, alcohols or diols having 1 to 4 carbon atoms are preferred, and ethanol is more preferred. The use of the obtained organic substance is not particularly limited. The obtained organic substance may be used as a raw material such as plastics or resin, or may be used as a solvent of any kind, bactericide or fuel. High-concentration ethanol is highly versatile. For example, it can be used as fuel ethanol to be mixed with gasoline or the like, as well as raw materials of cosmetics, beverages, chemical substances, fuels (jet fuels), or additives to foods.

Figure 4:
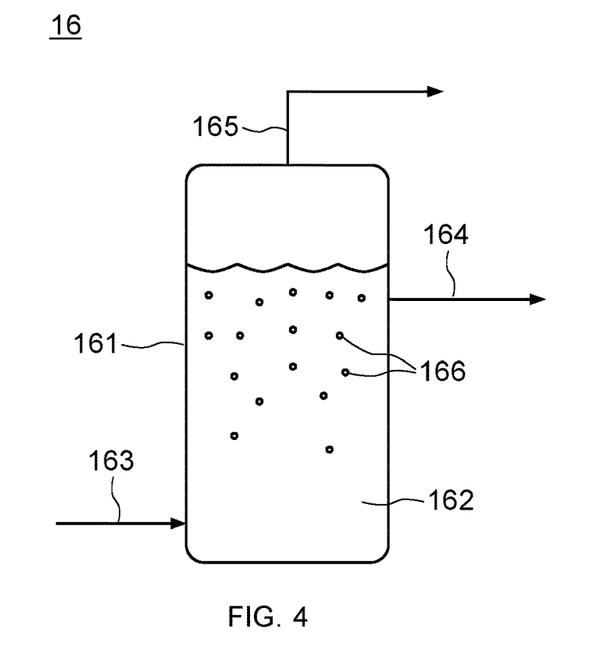
FIG. 4 is a view diagrammatically showing an organic-substance production apparatus of the gas treatment system of FIG. 1.

As shown in FIG. 4, for example, the organic-substance production apparatus 16 has a fermenter 161 containing microorganisms (species). The fermenter 161 may contain a medium (culture solution) 162 in addition to the microorganisms. A supply pipe 163 for supplying the source gas, a recovery pipe 164 for recovering an obtained organic substance, and a discharge pipe 165 for discharging a gas not used for generating the organic substance are connected to the organic-substance production apparatus 16. In FIG. 4, a reference numeral 166 represents bubbles 166 in the culture solution 162. The bubbles 166 mainly contain a gas that has not been used for generating the organic substance. The bubbles 166 contain nitrogen and carbon dioxide, for example. The bubbles 166 rise to a liquid surface of the medium (culture solution) 162, and are then discharged through the discharge pipe 165.

It is known that certain anaerobic microorganisms produce by fermentation an organic substance as a valuable resource, such as ethanol, from a substrate gas such as a source gas. Gas-utilizing microorganisms of this type are cultured in a liquid medium. For example, a culture solution and gas-utilizing bacteria may be supplied into a fermenter, and a source gas may be supplied to the fermenter, while the culture solution housed in the fermenter is stirred. Thus, the gas-utilizing bacteria can be incubated in the culture solution, and an organic substance can be produced by its fermentation action from the source gas. The culture solution is a liquid containing water as a main component, and nutrients (e.g., vitamin, phosphoric acid, etc.) dissolved or dispersed in the water. A composition of such a culture solution is prepared such that the gas-utilizing bacteria can grow well.

Microorganisms (species) that ferment the source gas with microorganisms are not particularly limited, as long as they can manufacture a desired organic substance by fermenting the source gas with microorganisms with the use of hydrogen and carbon monoxide as main raw materials. For example, the microorganisms (species) preferably produce an organic substance from a source gas by a fermentation action of gas-utilizing bacteria. Among the gas-utilizing bacteria, the genus *Clostridium* is more preferred, and *Clostridium autoethanogenum* is particularly preferred, but the present invention is not limited thereto. Herebelow, examples are further shown.

The gas-utilizing bacteria include both eubacteria and ancient bacteria. Examples of the eubacteria may include bacteria of the genus *Clostridium*, bacteria of the genus *Moorella*, bacteria of the genus *Acetobacterium*, bacteria of the genus *Carboxydocella*, bacteria of the genus *Rhodopseudomonas*, bacteria of the genus *Eubacterium*, bacteria of the genus *Butyribacterium*, bacteria of the genus *Oligotropha*, bacteria of the genus *Bradyrhizobium*, bacteria of the genus *Ralsotonia* which are aerobic hydrogen oxidizing bacteria, etc.

On the other hand, examples of the ancient bacteria may include bacteria of the genus *Methanobacterium*, bacteria of the genus Methanobrevibacter, bacteria of the genus *Methanocalculus*, bacteria of the genus Methanococcus, bacteria of the genus *Methanosarcina*, bacteria of the genus *Methanosphaera*, bacteria of the genus *Methanothermobacter*, bacteria of the genus *Methanothrix*, bacteria of the genus *Methanoculleus*, bacteria of the genus *Methanofollis*, bacteria of the genus *Methanogenium*, bacteria of the genus *Methanospirillium*, bacteria of the genus *Methanosaeta*, bacteria of the genus *Thermococcus*, bacteria of the genus *Thermofilum*, bacteria of the genus *Arcaheoglobus*, etc. Among these ancient bacteria, bacteria of the genus *Methanosarcina*, bacteria of the genus Methanococcus, bacteria of the genus *Methanothermobacter*, bacteria of the genus *Methanothrix*, bacteria of the genus *Thermococcus*, bacteria of the genus *Thermofilum*, and bacteria of the genus *Archaeoglobus* are preferred.

Further, as the ancient bacteria, bacteria of the genus *Methanosarcina*, bacteria of the genus *Methanothermobactor*, or bacteria of the genus Methanococcus are preferred, and bacteria of the genus *Methanosarcina* or bacteria of the genus Methanococcus are particularly preferred, because they are excellent in utilizing carbon monoxide and carbon dioxide. For example, *Methanosarcina* bacteria may be *Methanosarcina barkeri, Methanosarcina mazei, Methanosarcina acetivorans*, etc.

Bacteria having a high ability of generating a desired organic substance is selected and used from among the aforementioned gas-utilizing bacteria. Examples of bacteria having a high ability of generating ethanol may include *Clostridium autoethanogenum, Clostridium ljungdahlii, Clostridium aceticum, Clostridium carboxidivorans, Moorella thermoacetica, Acetobacterium woodii*, etc.

A medium used for culturing the aforementioned microorganisms (species) is not particularly limited, as long as it has an appropriate composition suitable for bacteria. For example, refer to US2017/260552A, paragraphs 0097 to 0099, about a medium when the genus *Clostridium* is used as microorganisms.

A temperature (culture temperature) of the medium (culture solution) in the fermenter is optional, but may be preferably about 30 to 45° C., more preferably about 33 to 42° C., further preferably about 36.5 to 37.5° C. A culturing time is preferably, in continuous culturing, 12 hours or more, more preferably 7 days or more, particularly preferably 30 days or more, most preferably 60 days or more. An upper limit thereof is not particularly set, but may be preferably 720 days or less, more preferably 365 days or less, from the viewpoint of regular maintenance of an installation. The culturing time means a period from a time at which an inoculum is added to a culture tank to a time at which a culture solution in the culture tank is completely discharged.

When a metal catalyst is used in a reactor, a known metal catalyst used to obtain a desired organic substance from the source gas can be employed. For example, a metal catalyst containing one or more platinum group elements selected from ruthenium, rhodium, palladium, osmium, iridium and platinum is preferred from the viewpoint of increasing a CO conversion rate.

Next, the organic-substance refining apparatus 18 is described. The organic-substance refining apparatus 18 is an apparatus that refines an organic-substance containing liquid obtained through microbial fermentation in the organic-substance production apparatus 16. For example, the organic-substance refining apparatus 18 separates, in a refining unit, the obtained organic-substance containing liquid into a distillate liquid having an increased concentration of the desired organic substance, and a residual liquid having a lowered concentration of the desired organic substance. Examples of such an organic-substance refining apparatus 18 may include a distillation apparatus, a treatment apparatus including a permeation vaporization membrane, a treatment apparatus including a zeolite dehydration membrane, a treatment apparatus for removing a low-boiling point substance having a boiling point lower than that of the organic substance, a treatment apparatus for removing a high-boiling point substance having a boiling point higher than that of the organic substance, a treatment apparatus including an ion exchange membrane, etc. One of these apparatuses may be used alone, or two or more of these apparatuses may be used in combination. Thermal distillation or membrane separation may be suitably used as a unit operation.

In thermal distillation, a distillation apparatus can be used. A temperature in a distiller during distillation of an organic substance (in particular, ethanol) is not particularly limited, but is preferably 100° C. or less, more preferably about 70 to 95° C. The aforementioned temperature range in the distiller allows more reliable separation of a necessary organic substance from other components, i.e., distillation (refinement) of the organic substance.

A pressure in the distillation apparatus during distillation of the organic substance may be a normal pressure, but is preferably less than an atmospheric pressure, more preferably about 60 to 95 kPa (absolute pressure). The aforementioned pressure range in the distillation apparatus allows a separation efficiency of the organic substance and thus a yield of the organic substance to be improved. A yield of the organic substance (a concentration of the organic substance obtained after distillation) is preferably 90% by weight or more, more preferably 99% by weight or more, in particular, 99.5% by weight or more.

In membrane separation, a known separation film can be suitably used. For example, a zeolite membrane can be preferably used.

In this manner, the gas treatment system 10 can manufacture an organic substance from a source gas.

Concentrations of respective gases contained in the source gas produced by the source-gas production apparatus 12 may vary. For example, such a case occurs when a carbon source is not constant, and/or when a reaction performed by the source-gas production apparatus 12 is not uniform, for example. As described above, in the organic-substance production apparatus, such as a culture tank, which produces an organic substance from a source gas, bubbles are likely to generate on a liquid surface because of a reaction. When an amount of an inert gas in the source gas increases in such a situation, bubbles may generate albeit temporarily. Such bubbles may enter an apparatus downstream of the organic-substance production apparatus, which may cause failure and/or contamination. This tendency may be remarkable in waste in which a carbon source is not uniform, such as plastic waste, garbage, municipal waste (MSW), waste tires, biomass waste, household waste such as blankets and paper, in particular, plastic waste, garbage, municipal waste (MSW), waste tires, in more particular, municipal waste (MSW).

This embodiment observes a total concentration of a carbon dioxide concentration and a nitrogen concentration in a source gas, and prevents or suppresses bubbles by ability regulation that enhances an ability to reduce a carbon dioxide concentration. Since carbon dioxide and nitrogen are not used at all or rarely used for producing an organic substance, they directly contribute to generation of bubbles in the fermenter 161, and have no or little effect on production of an organic substance. Thus, generation of bubbles can be easily prevented or suppressed by observing them. Further, since a carbon dioxide concentration can be more easily regulated by the adsorption apparatus, this embodiment controls particularly the carbon dioxide concentration. This can prevent or suppress generation of bubbles.

In more detail, a carbon dioxide concentration and a nitrogen concentration before they are passed through the adsorption unit, or a carbon dioxide concentration and a nitrogen concentration after they have been passed through the adsorption unit are monitored. A carbon dioxide concentration and a nitrogen concentration can be monitored both before they are passed through the adsorption unit and after they have been passed through the adsorption unit. When a total concentration of the monitored carbon dioxide concentration and the nitrogen concentration exceeds a threshold value, the ability of the adsorption unit to reduce a carbon dioxide concentration in the source gas is enhanced so as to reduce the carbon dioxide concentration. Thus, the total concentration of the carbon dioxide concentration and the nitrogen concentration can be reduced to suppress generation of bubbles. In this specification, the "threshold value" usually means that it is 5% or more higher than a total concentration (% by volume) of a carbon dioxide concentration (% by volume) and a nitrogen concentration (% by volume) in the source gas. At this time, "a total concentration (% by volume) of a carbon dioxide concentration (% by volume) and a nitrogen concentration (% by volume) contained in the source gas" means an average value during the source gas is continuously produced from a carbon source for 24 hours. The structure of the adsorption apparatus 50 is described in detail herebelow.

In this embodiment, as shown in FIG. 3, the adsorption apparatus 50 has the monitoring unit 56 that monitors a carbon dioxide concentration and a nitrogen concentration in the source gas. In the example shown in FIG. 3, the monitoring unit 56 is provided on the outlet unit 54 downstream of the adsorption unit 52. In this case, the monitoring unit 56 monitors a carbon dioxide concentration and a nitrogen concentration in the source gas after having passed through the adsorption unit 52.

In this embodiment, when a total concentration of a carbon dioxide concentration and a nitrogen concentration in the source gas exceeds a threshold value, the control unit 55 of the adsorption unit 50 controls the inlet unit 51 and the outlet unit 54 to shorten a switching cycle of the adsorption process and the regeneration process which are alternately performed by the first adsorption unit 521 and the second adsorption unit 522. This can enhance the ability of the adsorption unit 52 to reduce a carbon dioxide concentration in the source gas (referred to as carbon-dioxide removal ability herebelow). Thus, the carbon dioxide concentration in the source gas after having passed through the adsorption unit 52 can be reduced. The reason why the carbon-dioxide removal ability of the adsorption unit 52 can be increased by shortening the switching cycle of the adsorption process and the regeneration process is described later.

Among gases in the source gas supplied to the organic-substance generation apparatus 16, main components of gases which are not used at all or rarely used for producing of an organic substance are nitrogen and carbon dioxide. Thus, even when a nitrogen concentration in the source gas increases, an increase in total amount of gases not used for producing an organic substance can be suppressed by enhancing the carbon-dioxide removal ability of the adsorption unit 52 to reduce a carbon dioxide concentration in the source gas. This can suppress generation of bubbles on the liquid surface of the medium (culture solution) 162.

Next, a method of treating a source gas by using the gas treatment apparatus 12 as structured above is described.

After the scrubber 30, the gas piping apparatus 40, etc. have treated the source gas produced by the source-gas generation apparatus 12, the gas treatment apparatus 14 leads the source gas into the adsorption apparatus 50. The adsorption apparatus 50 performs an adsorption step of passing the source gas through the adsorption unit 52 to reduce a carbon dioxide concentration in the source gas.

In the adsorption step, the first adsorption unit 521 and the second adsorption unit 522 of the adsorption unit 52 alternately perform the adsorption process and the regeneration process. For example, the control unit 55 switches the inlet-side switching unit 511 of the inlet unit 51 in a first switching cycle T1, such that the pressurized source gas is lead alternately into the first adsorption unit 521 and the second adsorption unit 522. In addition, the control unit 55 switches the outlet-side switching unit 541 of the outlet unit 54 in the first switching cycle T1, such that the source gas after having passed through the first adsorption unit 521 or the second adsorption unit 522 where the adsorption process is performed is lead downstream.

Figure 5:
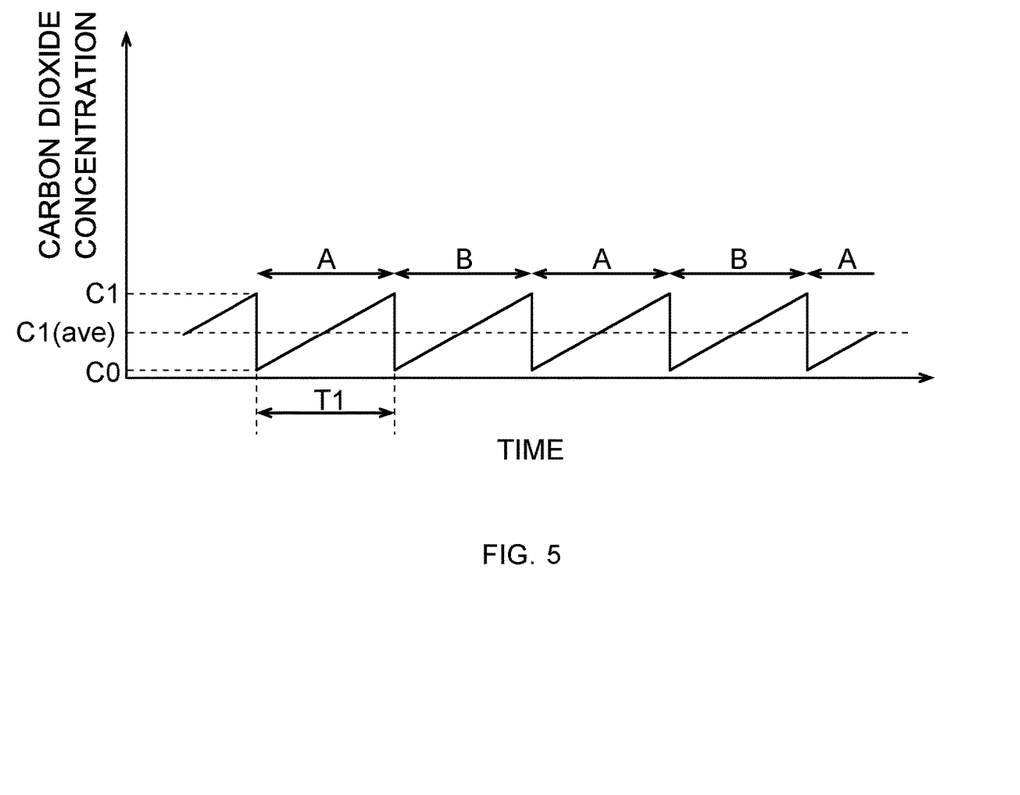
FIG. 5 is a view for describing an example of a control method of the adsorption apparatus.

FIG. 5 is a view showing a carbon dioxide concentration in the source gas after having passed through the adsorption unit 52, when the adsorption process and the regeneration process are switched in the first switching cycle T1. In FIG. 5, the first adsorption unit 521 performs the adsorption process during a period shown by an arrow A, and the second adsorption unit 522 performs the adsorption process during a period shown by an arrow B.

An ability of the adsorbent 53 to adsorb carbon dioxide is highest immediately after the adsorption process started following to the regeneration process. Thereafter, as the adsorption process continues, the ability of the adsorbent 53 to adsorb carbon dioxide gradually lowers. Thus, as shown in FIG. 5, the carbon dioxide concentration in the source gas after having passed through the adsorption unit 52 is lowest immediately after the first adsorption unit 521 or the second adsorption unit 522 started the adsorption process. A reference numeral C0 is a carbon dioxide concentration immediately after the the first adsorption unit 521 or the second adsorption unit 522 started the adsorption process. C0 is about 0% by volume, for example. A reference numeral C1 is a carbon dioxide concentration immediately before the first adsorption unit 521 or the second adsorption unit 522 finishes the adsorption process, when the adsorption process and the regeneration process are switched in the first switching cycle T1. C1 is about 20% by volume, for example. An average value C1(ave) of concentrations of the carbon dioxide in the source gas after having passed through the adsorption unit 52 is an intermediate value between the concentration C0 and the concentration C1. C1(ave) is about 10% by volume, for example.

The source gas subjected to the adsorption step in the adsorption unit 52 is sent to the supply apparatus 60 through the outlet unit 54. The supply apparatus 60 supplies the source gas whose carbon dioxide concentration has been reduced by the adsorption step to the organic-substance generation apparatus 16.

During the adsorption step, the monitoring unit 56 performs a monitoring step of monitoring a carbon dioxide concentration and a nitrogen concentration in the source gas after having passed through the adsorption unit 52. The nitrogen concentration in the source gas is 10% by volume, for example.

During the adsorption step, the control unit 55 of the adsorption apparatus 50 determines whether a total concentration of the carbon dioxide concentration and the nitrogen concentration monitored in the monitoring step exceeds a threshold value. The threshold value can be varied depending on a liquid level of the medium (culture solution) 162 in the fermenter 161. The threshold value is preferably within a range between 10 and 20% by volume, for example, 15% by volume.

When a total concentration of the carbon dioxide concentration and the nitrogen concentration monitored in the monitoring step exceeds a threshold value, the control unit 55 performs an ability regulating step of enhancing the carbon-dioxide removal ability of the adsorption unit 52. To be specific, the control unit 55 changes the switching cycle in which the adsorption process and the regeneration process are alternately performed by the first adsorption unit 521 and the second adsorption unit 522, from the first switching cycle T1 to a second switching cycle T2 shorter than the first switching cycle T1. The second switching cycle T2 is, for example, ⅘ or less of the first switching cycle T1. Alternatively, the second switching cycle T2 may be either ⅗ or less of the first switching cycle T1, or ⅖ or less of the first switching cycle T1.

Figure 6:
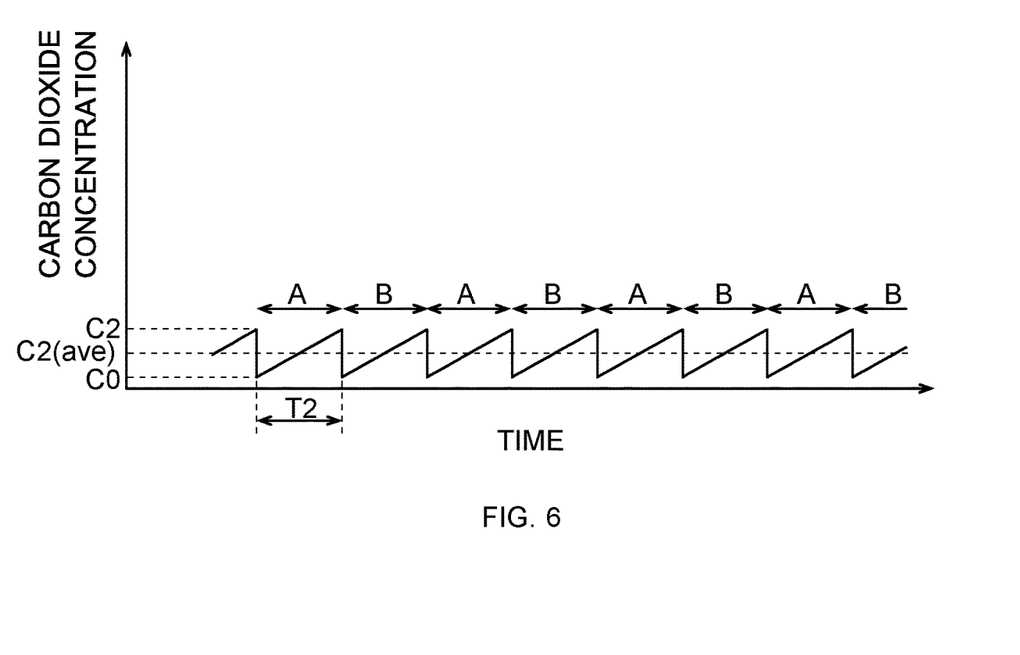
FIG. 6 is a view for describing an example of the control method of the adsorption apparatus.

Herebelow, the reason why the carbon-dioxide removal ability of the adsorption unit 52 is enhanced by shortening the switching cycle of the adsorption process and the regeneration process is described with reference to FIG. 6. FIG. 6 is a view showing a carbon dioxide concentration in the source gas after having passed through the adsorption unit 52, when the adsorption process and the regeneration process are switched in the second switching cycle T2 which is shorter than the first switching cycle T1. As is the case for FIG. 5, in FIG. 6, the first adsorption unit 521 performs the adsorption process during a period shown by an arrow A, and the second adsorption unit 522 performs the adsorption process during a period shown by an arrow B.

As described above, the ability of the adsorbent 53 to adsorb carbon dioxide is highest immediately after the adsorption process started following to the regeneration process, and thereafter the ability gradually lowers. In the example shown in FIG. 6, the adsorption process and the regeneration process are switched in the second switching cycle T2 which is shorter than the first switching cycle T1. Thus, as shown in FIG. 6, the ability of the adsorption unit 53 to adsorb carbon dioxide immediately before the first adsorption unit 521 or the second adsorption unit 522 finishes the adsorption process is higher than that of a case in which the adsorption process and the regeneration process are switched in the first switching cycle T1. As a result, a carbon dioxide concentration C2 immediately before the first adsorption unit 521 or the second adsorption unit 522 finishes the adsorption process in the example shown in FIG. 6 is lower than the carbon dioxide concentration C1 in the example shown in FIG. 5. For example, the concentration C2 is about 10% by volume. In this case, an average value C2(ave) of concentrations of the carbon dioxide in the source gas after having passed through the adsorption unit 52 is an intermediate value between the concentration C0 and the concentration C2. C2(ave) is about 5% by volume, for example. As can be seen, an average value of concentrations of the carbon dioxide in the source gas after having passed through the adsorption unit 52 can be lowered by shortening the switching cycle of the adsorption process and the regeneration process. Namely, the carbon-dioxide removal ability of the adsorption unit 52 can be enhanced by shortening the switching cycle of the adsorption process and the regeneration process.

In this manner, according to this embodiment, the carbon-dioxide removal ability of the adsorption unit 52 can be enhanced by changing the switching cycle of the adsorption process and the regeneration process from the cycle T1 to the cycle T2. Thus, a carbon dioxide concentration in the source gas after having passed through the adsorption unit 52 can be lowered as compared with a case in which the adsorption unit 52 is controlled in the first switching cycle T1. Thus, even when a total concentration of the carbon dioxide concentration and the nitrogen concentration in the source gas increases, the total concentration can become a lower value by reducing the carbon dioxide concentration. This can suppress formation of bubbles on a liquid surface of the medium (culture solution) 162 in the organic-substance generation apparatus 16.

Thereafter, when the total concentration of the carbon dioxide concentration and the nitrogen concentration monitored in the monitoring step falls below the threshold value, the control unit 55 may return the switching cycle of the adsorption process and the regeneration process from the cycle T2 to the cycle T1.

The aforementioned embodiment can be variously modified. Modification examples are described herebelow with reference to the drawings according to need. In the following description and the drawings used therein, the same reference numerals as those used for the corresponding parts in the aforementioned embodiment are used for the parts that can be configured in the same manner as in the aforementioned embodiment, and duplicate description is omitted. Further, when the same effect obtained in the aforementioned embodiment can be clearly obtained, the description may be omitted.

First Modification Example

Figure 7:
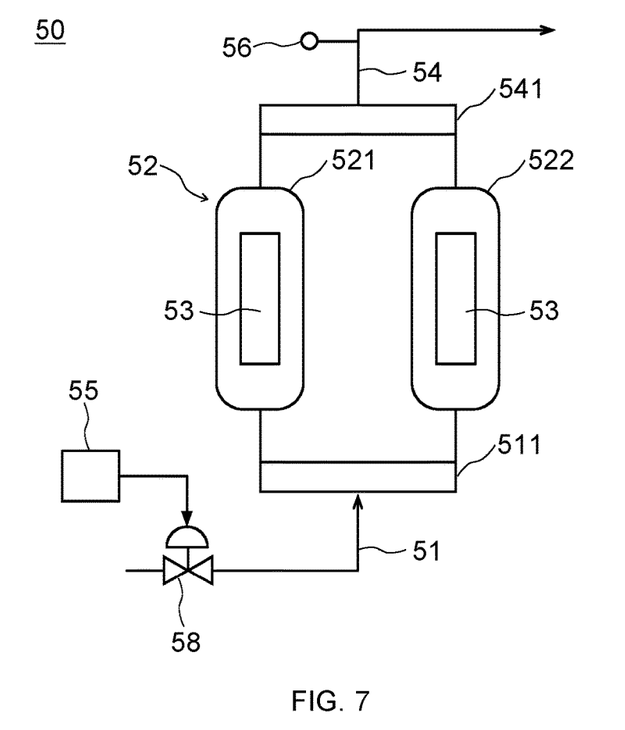
FIG. 7 is a view diagrammatically showing a modification example of the adsorption apparatus.

In this modification example, an example in which the carbon-dioxide removal ability of the adsorption unit 52 is regulated by regulating a flow rate of a source gas to be supplied to the adsorption unit 52 is described. FIG. 7 is a view showing an adsorption apparatus 50 in this modification example.

As shown in FIG. 7, the adsorption apparatus 50 has a flow-rate regulation unit 58 that regulates a flow rate of a source gas to be supplied by the inlet unit 51 to the adsorption unit 52. The flow-rate regulation unit 58 is a throttle valve, for example. The flow-rate regulation unit 58 is controlled by the control unit 55.

When a total concentration of the carbon dioxide concentration and the nitrogen concentration monitored in the monitoring step exceeds a threshold value, the control unit 55 performs the ability regulation step of enhancing the carbon-dioxide removal ability of the adsorption unit 52. In this modification example, the control unit 55 lowers a flow rate of the source gas to be supplied to the adsorption unit 52.

Figure 8:
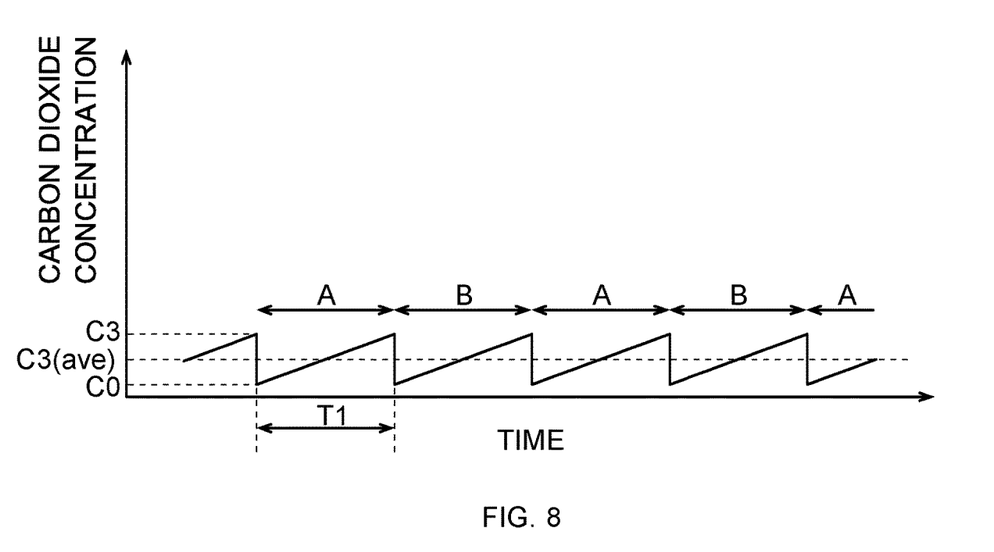
FIG. 8 is a view for describing an example of the control method of the adsorption apparatus.

The reason why the carbon-dioxide removal ability of the adsorption unit 52 can be increased by lowering a flow rate of the source gas to be supplied to the adsorption unit 52 is described herebelow with reference to FIG. 8. FIG. 8 is a view showing a carbon dioxide concentration in the source gas after having passed through the adsorption unit 52, when the source gas is supplied to the adsorption unit 52 at a flow rate lower than that of the aforementioned embodiment shown in FIG. 5. Also in FIG. 8, the first adsorption unit 521 performs the adsorption process during a period shown by an arrow A, and the second adsorption unit 522 performs the adsorption process during a period shown by an arrow B.

As described above, the ability of the adsorbent 53 to adsorb carbon dioxide is highest immediately after the adsorption process started following to the regeneration process, and thereafter the ability gradually lowers. The ability lowering degree corresponds to a cumulative amount of the carbon dioxide absorbed by the adsorbent 53. Thus, in a case where the adsorption process and the regeneration process are switched in the first switching cycle T1 as in the case shown in FIG. 5, since a flow rate of the source gas to be supplied to the adsorption unit 52 is low, a cumulative amount of the carbon dioxide adsorbed by the adsorbent is small, whereby the lowering degree of the ability of the adsorbent 53 to adsorb carbon dioxide is small. Thus, a carbon dioxide concentration C3 immediately before the first adsorption unit 521 or the second adsorption unit 522 finishes the adsorption process in the example shown in FIG. 8 is lower than the carbon dioxide concentration C1 in the example shown in FIG. 5. In this case, an average value C3(ave) of concentrations of the carbon dioxide in the source gas after having passed through the adsorption unit 52 is an intermediate value between the concentration C0 and the concentration C3. C3(ave) is about 5% by volume, for example.

In this manner, the carbon-dioxide removal ability of the adsorption unit 52 can be enhanced by lowering a flow rate of the source gas to be supplied to the adsorption unit 52. Thus, even when a total concentration of the carbon dioxide concentration and the nitrogen concentration in the source gas increases, the total concentration can become a lower value by reducing the carbon dioxide concentration. This can suppress formation of bubbles on a liquid surface of the medium (culture solution) 162 in the organic-substance generation apparatus 16.

Second Modification Example

The aforementioned embodiment and the modification example describe the example in which the adsorption apparatus 50 is a separation apparatus of a pressure swing adsorption method (PSA). However, the adsorption apparatus 50 is not particularly limited to thereto. Although not shown, the adsorption apparatus 50 may be either a separation apparatus of a temperature swing adsorption method (TSA) or a separation apparatus of a pressure temperature swing adsorption method (PTSA). Regardless of method of the adsorption apparatus 50, formation of bubbles on a liquid surface of the medium (culture solution) 162 in the organic-substance generation apparatus 16 can be suppressed by regulating the carbon-dioxide removal ability of the adsorption apparatus 50 depending on a total concentration of the carbon dioxide concentration and the nitrogen concentration in the source gas.

Figure 9:
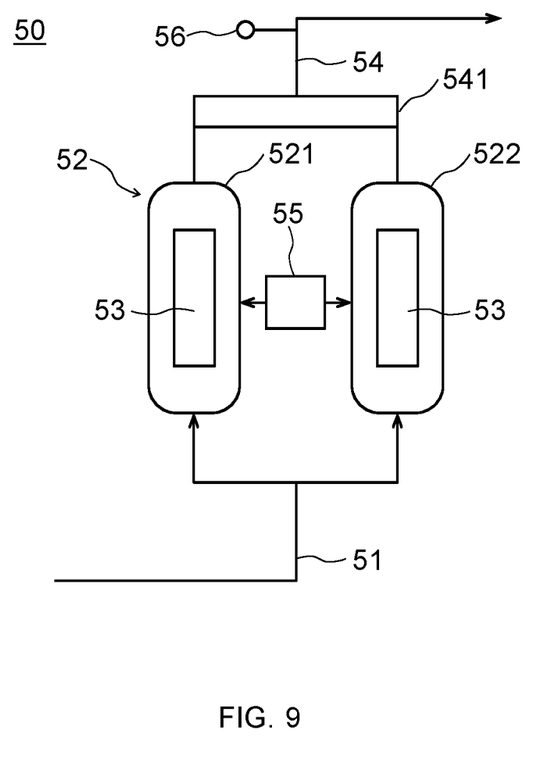
FIG. 9 is a view diagrammatically showing a modification example of the adsorption apparatus.

FIG. 9 is a view showing an example of the adsorption apparatus 50 formed as a separation apparatus of a temperature swing adsorption method (TSA). In the example shown in FIG. 9, the control unit 55 alternately raises temperatures of the first adsorption unit 521 and the second adsorption unit 522 so that the adsorption process and the regeneration process are alternately performed by the first adsorption unit 521 and the second adsorption unit 522. In addition, the carbon-dioxide removal ability of the adsorption apparatus 50 can be regulated by regulating a switching cycle of the adsorption process and the regeneration process, and/or by regulating a flow rate of the source gas to be supplied to the adsorption unit 52.

Third Modification Example

The aforementioned embodiment and the modification examples show the example in which the monitoring unit of the adsorption apparatus 50 is provided on the outlet unit 54 downstream of the outlet-side switching unit 541. Namely, a carbon dioxide concentration and a nitrogen concentration in the source gas after having passed through the adsorption unit 52 are monitored in the monitoring step. However, a position where a carbon dioxide concentration and a nitrogen concentration in the source gas are monitored is not particularly limited thereto. For example, although not shown, the monitoring unit 56 of the adsorption apparatus 50 may be provided on the inlet unit 51 upstream of the adsorption unit 52. In this case, a carbon dioxide concentration and a nitrogen concentration in the source gas before passing through the adsorption unit 52 are monitored in the monitoring step. Alternatively, a monitoring unit that monitors a carbon dioxide concentration and a nitrogen concentration in the source gas may be provided on the organic-substance production apparatus 16. In this case, a carbon dioxide concentration and a nitrogen concentration in the source gas having been supplied to the organic-substance production apparatus 16 are monitored in the monitoring step.

Some modification examples of the aforementioned embodiment have been described. It goes without saying that the modifications are suitably combined and used.

10 Gas treatment system
12 Source-gas production apparatus
14 Gas treatment apparatus
16 Organic-substance production apparatus
18 Organic-substance refining apparatus
20 Monitoring apparatus
30 Scrubber
40 Gas piping apparatus
50 Adsorption apparatus
51 Inlet unit
511 Inlet-side switching unit
52 Adsorption unit
521 First adsorption unit
522 Second adsorption unit
53 Adsorbent
54 Outlet unit
541 Outlet-side switching unit
55 Control unit
56 Monitoring unit
58 Flow-rate regulation unit
60 Supply apparatus

What is claimed is:

1. A gas treatment method comprising:
   an adsorption step of passing a source gas containing at least carbon dioxide and nitrogen through an adsorption unit housing an adsorbent for adsorbing carbon dioxide to reduce a carbon dioxide concentration in the source gas;
   a supply step of supplying the source gas whose carbon dioxide concentration has been reduced by the adsorption step to an organic-substance production apparatus that produces an organic substance; and
   a monitoring step of monitoring a carbon dioxide concentration and a nitrogen concentration in the source gas before passing through the adsorption unit, a carbon dioxide concentration and a nitrogen concentration in the source gas after having passed through the adsorption unit, or a carbon dioxide concentration and a nitrogen concentration in the source gas having been supplied to the organic-substance production apparatus;
   wherein the adsorption step has an ability regulation step of enhancing an ability of the adsorption unit to reduce a carbon dioxide concentration in the source gas, when a total concentration of the carbon dioxide concentration and the nitrogen concentration monitored in the monitoring step exceeds a threshold value.

2. The gas treatment method according to claim 1, wherein:
   the adsorption unit used in the adsorption step includes a first adsorption unit and a second adsorption unit that alternately perform an adsorption process for adsorbing carbon dioxide onto the adsorbent and a regeneration process for releasing the carbon dioxide adsorbed on the adsorbent, and
   the ability regulation step shortens a switching cycle of the adsorption process and the regeneration process that are alternately performed by the first adsorption unit and the second adsorption unit, when the total concentration of the carbon dioxide concentration and the nitrogen concentration monitored in the monitoring step exceeds the threshold value.

3. The gas treatment method according to claim 1, wherein:
   the adsorption unit used in the adsorption step includes a first adsorption unit and a second adsorption unit that alternately perform an adsorption process for adsorbing carbon dioxide onto the adsorbent and a regeneration process for releasing the carbon dioxide adsorbed on the adsorbent, and
   the ability regulation step lowers a flow rate of the source gas to be supplied to the adsorption unit including the first adsorption unit and the second adsorption unit, when the total concentration of the carbon dioxide concentration and the nitrogen concentration monitored in the monitoring step exceeds the threshold value.

4. The gas treatment method according to claim 1, wherein
   the source gas is a synthetic gas further containing hydrogen and carbon monoxide.

5. The gas treatment method according to claim 4, wherein
   the organic substance is produced from the carbon monoxide and the hydrogen as raw materials.

6. The gas treatment method according to claim 1, wherein
   the adsorption step reduces a carbon dioxide concentration in the source gas by a pressure swing adsorption method.

7. A gas treatment apparatus for a source gas containing at least carbon dioxide and nitrogen, comprising:
- an adsorption apparatus that reduces a carbon dioxide concentration in the source gas, the adsorption apparatus including an adsorption unit that houses an adsorbent for adsorbing carbon dioxide, an inlet unit that leads the source gas into the adsorption unit, and an outlet unit that leads the source gas out of the adsorption unit;
- a supply apparatus that supplies the source gas whose carbon dioxide concentration has been reduced by the adsorption apparatus to an organic-substance production apparatus that produces an organic substance;
- a monitoring unit that monitors a carbon dioxide concentration and a nitrogen concentration in the source gas before passing through the adsorption unit, or a carbon dioxide concentration and a nitrogen concentration in the source gas after having passed through the adsorption unit; and
- a control unit that controls the adsorption unit, the inlet unit or the outlet unit to enhance an ability of the adsorption unit to reduce a carbon dioxide concentration in the source gas, when a total concentration of the carbon dioxide concentration and the nitrogen concentration monitored by the monitoring unit exceeds a threshold value.

8. The gas treatment apparatus according to claim 7, wherein:
- the adsorption unit of the adsorption apparatus includes a first adsorption unit and a second adsorption unit that alternately perform an adsorption process for adsorbing carbon dioxide onto the adsorbent and a regeneration process for releasing the carbon dioxide adsorbed on the adsorbent; and
- the control unit shortens a switching cycle of the adsorption process and the regeneration process that are alternately performed by the first adsorption unit and the second adsorption unit, when the total concentration of the carbon dioxide concentration and the nitrogen concentration in the source gas before passing through the adsorption unit, the total concentration of the carbon dioxide concentration and the nitrogen concentration in the source gas after having passed through the adsorption unit, or a total concentration of a carbon dioxide concentration and a nitrogen concentration in the source gas having been supplied to the organic-substance production apparatus exceeds a threshold value.

9. The gas treatment apparatus according to claim 7, wherein:
- the adsorption unit of the adsorption apparatus includes a first adsorption unit and a second adsorption unit that alternately perform an adsorption process for adsorbing carbon dioxide onto the adsorbent and a regeneration process for releasing the carbon dioxide adsorbed on the adsorbent; and
- the control unit lowers a flow rate of the source gas to be supplied to the adsorption unit including the first adsorption unit and the second adsorption unit, when the total concentration of the carbon dioxide concentration and the nitrogen concentration in the source gas before passing through the adsorption unit, the total concentration of the carbon dioxide concentration and the nitrogen concentration in the source gas after having passed through the adsorption unit, or a total concentration of a carbon dioxide concentration and a nitrogen concentration in the source gas having been supplied to the organic-substance production apparatus exceeds a threshold value.

10. The gas treatment apparatus according to claim 7, wherein
- the adsorption unit reduces a carbon dioxide concentration in the source gas by a pressure swing adsorption method.

* * * * *